(12) United States Patent
Gagnon (10) Patent No.: US 6,455,856 B1
(45) Date of Patent: Sep. 24, 2002

(54) GAMMA CAMERA GANTRY AND IMAGING METHOD

(75) Inventor: Daniel Gagnon, Twinsburg, OH (US)

(73) Assignee: Koninklijke Philips Electronics N.V. (NL)

( * ) Notice: Subject to any disclaimer, the term of this patent is extended or adjusted under 35 U.S.C. 154(b) by 10 days.

(21) Appl. No.: 09/585,957

(22) Filed: Jun. 2, 2000

(51) Int. Cl.[7] .............................. G01T 1/164; G01T 1/20
(52) U.S. Cl. ................................. 250/366; 250/363.03
(58) Field of Search ........................... 250/366, 363.03, 250/363.04, 363.05, 363.8

(56) References Cited

U.S. PATENT DOCUMENTS

| | | | | |
|---|---|---|---|---|
| 4,645,933 A | * | 2/1987 | Gambini | 250/363.05 |
| 4,677,299 A | * | 6/1987 | Wong | 250/363.03 |
| 5,105,086 A | * | 4/1992 | Pierfitte et al. | 250/363.05 |
| 5,798,527 A | * | 8/1998 | Muehllehner et al. | 250/363.03 |
| 5,813,983 A | * | 9/1998 | DiFilippo et al. | 250/363.03 |
| 6,175,116 B1 | * | 1/2001 | Gagnon et al. | 250/363.03 |

* cited by examiner

*Primary Examiner*—Georgia Epps
*Assistant Examiner*—Alicia M Harrington
(74) *Attorney, Agent, or Firm*—John J. Fry; Eugene E. Clair (57) ABSTRACT

A gamma camera includes first and second detectors. The first detector is located beneath a patient receiving surface. The second detector is located above the patient receiving surface. The second detector is movable between operating and retracted positions. The second detector includes a plurality of discrete detector portions, each detector portion having a first radiation sensitive face which faces an examination region and a second radiation sensitive face. The patient receiving surface generates signals indicative of pressure applied to the patient receiving surface. A movable transmission radiation source provides transmission radiation, interactions between the transmission radiation and the second detector generating Compton scattered radiation at least a portion of which is received by the first detector, coincident radiation being used to generate a transmission attenuation map. The gamma camera also includes an ultrasound device.

25 Claims, 7 Drawing Sheets

GAMMA CAMERA GANTRY AND IMAGING METHOD

BACKGROUND

The present invention relates to the nuclear medicine art. It finds particular application in conjunction with gamma cameras for positron and single photon imaging and will be described with particular reference thereto. It will also be appreciated that the present invention finds application to non-invasive inspection, industrial testing, and like applications.

Traditional nuclear cameras have included one or more radiation sensitive detectors. In single photon emission computed tomography (SPECT) systems, the detectors have been mounted for rotation about an examination region. As the detectors are rotated around the subject or indexed to a multiplicity of angularly offset positions around the subject, a tomographic data set indicative of a plurality of radionuclide decays occurring within the examination region is collected. This collected data is used to create a human-readable image indicative of the radionuclide spatial and temporal distribution.

Positron emission tomography (PET) scanners typically include ring of radiation sensitive detectors surrounding a central examination region. Positron annihilation events occurring within the examination region generate 511 keV gamma ray pairs travelling in opposite directions along a line of coincidence. Coincident gamma ray pairs detected by the ring of detectors are used to generate a human readable image indicative of the positron annihilation events.

More recently, gamma cameras capable of detecting both single photon radiation and positron annihilation events have been introduced. These cameras typically include a relatively thicker scintillator so that the 511 keV gamma rays characteristic of positron annihilation events can be more efficiently detected. Moreover, such cameras typically include coincidence logic for determining whether events are detected by two detectors substantially simultaneously.

While the foregoing devices have proven clinically and commercially successful, there remains room for improvement. For example, an increasing emphasis on improved imaging coverage and reduced imaging time leads to detector arrangements having a tunnel effect which limits access to the object under examination and which can be disconcerting to human patients. Moreover, ingress to and egress from such systems can be difficult. Dedicated PET scanners have been relatively expensive and confined to producing images indicative of relatively limited axial extent. Depending on the axial range over which data must be collected, it is often necessary to index the object with respect to the detectors and repeat the data collection procedure.

One factor affecting the quality of nuclear images has been non-uniform radiation attenuation in the object under examination. For example, some of the gamma radiation indicative of radionuclide decays occurring within the anatomy of a patient may travel through relatively attenuative material such as bone, whereas some of the radiation may not. If not corrected, this non-uniformity can result in undesirable image artifacts. As a result, gamma cameras have included transmission radiation sources. The transmission data has been used to generate attenuation maps of the object under examination. The attenuation maps have in turn been used to correct the received emission data.

However, coordination of single photon imaging with positron coincidence imaging has proven difficult. One alternative has been to obtain successive transmission and emission scans. Drawbacks to this approach include increased imaging time and possible misregistration of the transmission and emission date due to patient movement. Positron coincidence and transmission data have also been collected simultaneously. A drawback to this approach is the complexity inherent in operating a gamma camera in both single photon and coincidence modes simultaneously.

SUMMARY

Those skilled in the art will, upon reading and understanding the appended description, appreciate that aspects of the present invention address these and other matters.

According to a first aspect of the present invention, a gamma camera includes a fixed detector having a radiation sensitive face which faces an examination region and a movable second detector. The second detector includes a plurality of discrete detector portions each having a radiation sensitive face which faces the examination region. The second detector is movable between a first position opposite the examination region from the fixed detector for detecting radiation from the examination region and a second position for facilitating ingress of an object into the examination region.

According to a more limited aspect of the present invention, the discrete detector portions include an elongate scintillator, a plurality of photodetectors disposed along a first edge of the scintillator, and a plurality of photodetectors disposed along a second edge of the scintillator. The second edge of the scintillator, is opposite the first edge.

According to a still more limited aspect of the present invention, the elongate scintillator comprises a plurality of scintillator layers. The gamma camera includes photodetector means for detecting scintillations occurring in each of the layers.

According to another more limited aspect of the present invention, the gamma camera includes first and second moment processors operatively connected to the photodetectors for determining x,y positions of the scintillations.

According to another limited aspect, the gamma camera includes a transmission radiation source which emits radiation which interacts with the second detector to produce Compton scattered photons. At least a portion of the photons pass through the examination region and are received by the first detector. In its first position, the second detector is disposed between the transmission source and the examination region.

According to a more limited aspect, the gamma camera includes means for translating the transmission radiation source along each of the discrete detector portions.

According to a more limited aspect, the transmission radiation source includes one of 133-Ba and 137-Cs.

The gamma camera may also include a coincidence detector for determining whether radiation detected by the fixed detector and the detector portions of the second detector is coincident.

The gamma camera may also include a pressure sensitive surface disposed between the fixed detector and examination region which surface provides a signal indicative of a pressure applied to the surface. Means for determining a region of the object which can be modeled as a uniform medium and means for generating an attenuation map of a second region of the object can also be included.

According to another aspect of the present invention, a gamma camera includes a first detector having a radiation sensitive face which faces an examination region and a second detector disposed opposite the examination region from the first detector. The second detector includes a first radiation sensitive face which faces the examination region and a second radiation sensitive face. The camera also includes a transmission radiation source for emitting transmission radiation which is received by the second radiation sensitive face of the second detector, said transmission radiation interacting with the second detector to produce Compton scattered photons which are received by the first detector. Means for determining whether transmission radiation received by the second detector and Compton scattered photons received by the first detector are coincident is also included.

According to a more limited aspect, the second detector may include a plurality of elongate detector portions disposed in an arc about the examination region. The detector portions include a scintillator and a plurality of photodetectors for receiving light which has reached first and second edges of the scintillator.

The second detector may also include a scintillator having a plurality of layers and a plurality of photodectors for receiving signals indicative of scintillations occurring in each of the layers. The gamma camera further includes means for selectively disregarding signals from at least one of the layers during operation of the transmission radiation source.

According to a yet more limited aspect of the invention, the gamma camera may include a first scintillator layer disposed between a pair of light reflective surfaces which cause light generated within the crystal to be reflected to an edge thereof.

The gamma camera may include means for disregarding signals from a scintillator layer nearest the examination region while accepting signals from a layer nearest the transmission source.

According to another limited aspect of the invention, the second detector may be movable between a first position for detecting radiation from the examination region and a second position for facilitating ingress of an object into the examination region.

According to a still more limited aspect, the gamma camera may include means for scanning the transmission source across the second radiation sensitive face of the second detector when the second detector is in the first position.

According to a yet more limited aspect, the gamma camera may include means for scanning the transmission source longitudinally with respect to the examination region when the second detector is in the second position.

According to another aspect of the present invention, a method includes using a fixed radiation sensitive detector to detect gamma radiation from an examination region, using a second detector to delete gamma radiation from the examination region, determining whether the radiation detected by the first and second detectors is indicative of positron annihilation events, and generating an image indicative of the detected positron annihilation events. The second detector includes a plurality of discrete detector portions each having a first radiation sensitive face which faces the examination and is movable between a first position for detecting radiation from the examination region and a second position for facilitating ingress of an object into the examination region.

According to a limited aspect of the invention, the discrete detector portions include a second radiation sensitive face. The method includes the steps of providing transmission radiation which is received by the second radiation sensitive face of a discrete detector portion, said transmission radiation interacting with the discrete detector portion to produce Compton scattered photons which interact with the first detector, using the discrete detector portion to detect the interactions, using the first detector to detect radiation incident thereon, determining whether radiation received by the discrete detector portion and Compton scattered photons received by the first detector are coincident, and using the coincident radiation to provide an attenuation corrected image of the detected positron annihilation events.

The method may include repeating the steps of providing, using the discrete detector portion, using the first detector, and determining for a plurality of the discrete detector portions.

DRAWINGS

The invention may take form in various components and arrangements of components, and in various steps and arrangements of steps. The drawings are only for purposes of illustrating a preferred embodiment and are not to be construed as limiting the invention.

DESCRIPTION

Figure 1:
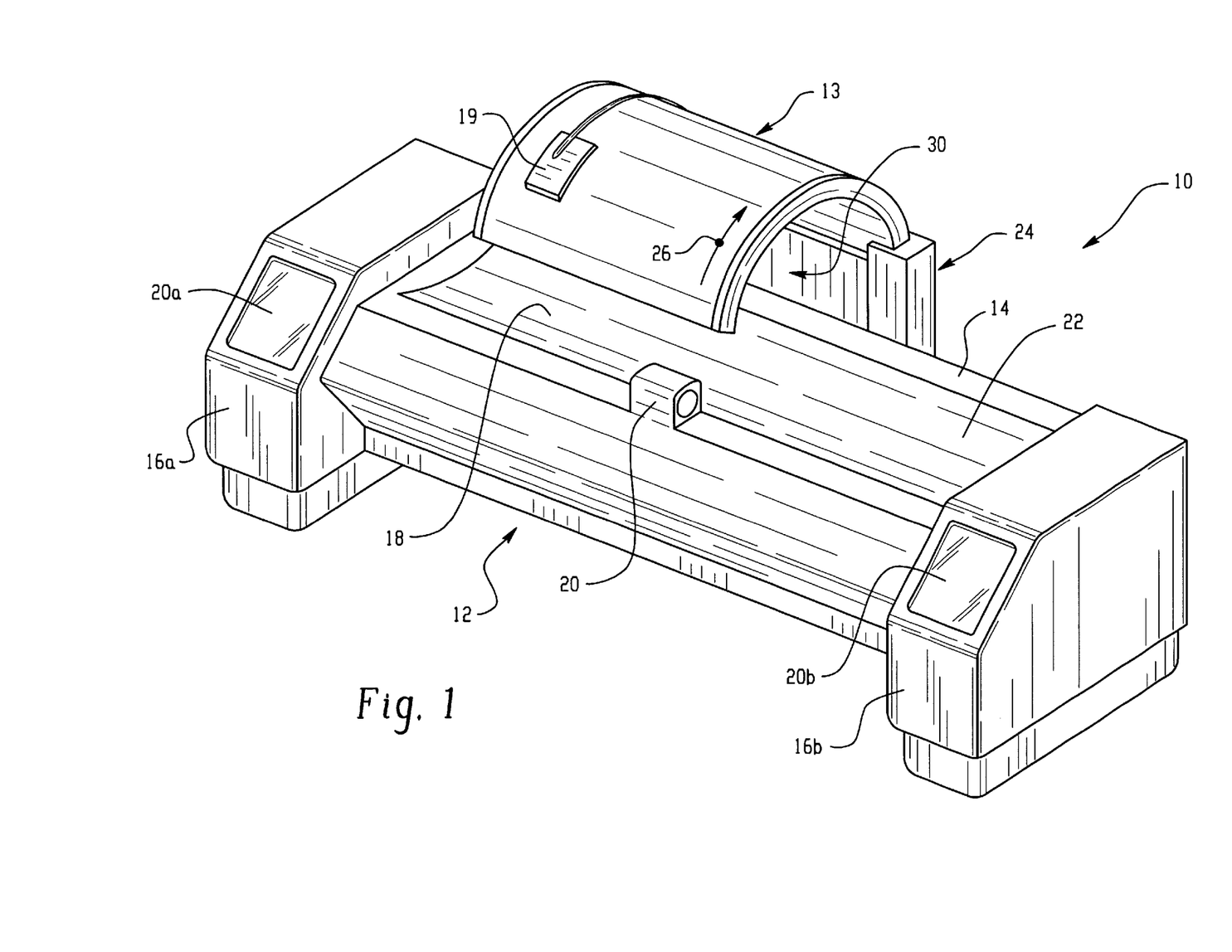
FIG. 1 is a perspective view of a gamma camera according to the present invention.

With reference to FIG. 1, a gamma camera 10 includes a lower gantry 12 and an upper detector 13. The lower gantry includes a object or patient support 14 having a curved object receiving surface 22. The patent support 14 is disposed between support pedestals 16a, 16b. Pertinent operator interface devices 20b, 20b such as monitors or other displays and operating controls may be mounted to one or both of the pedestals 16a, 16b or in another convenient location. Associated with the patient support 14 is a lower detector 18 and an injection and monitoring device 20. The upper 13 and lower 18 detectors each have radiation sensitive faces which receiving gamma radiation from an examination region 30. The lower detector 18 is mounted below the object receiving surface 22. While FIG. 1 depicts the upper detector 13 in its operating position, the upper detector is movable into storage unit 24 as generally depicted by arrow 26 so that the upper detector 13 may be retracted as needed, for example when not in use or for object ingress and egress. The gamma camera 10 also includes a transmission radiation source 19 and an ultrasound device (see FIG. 8).

Figure 2:
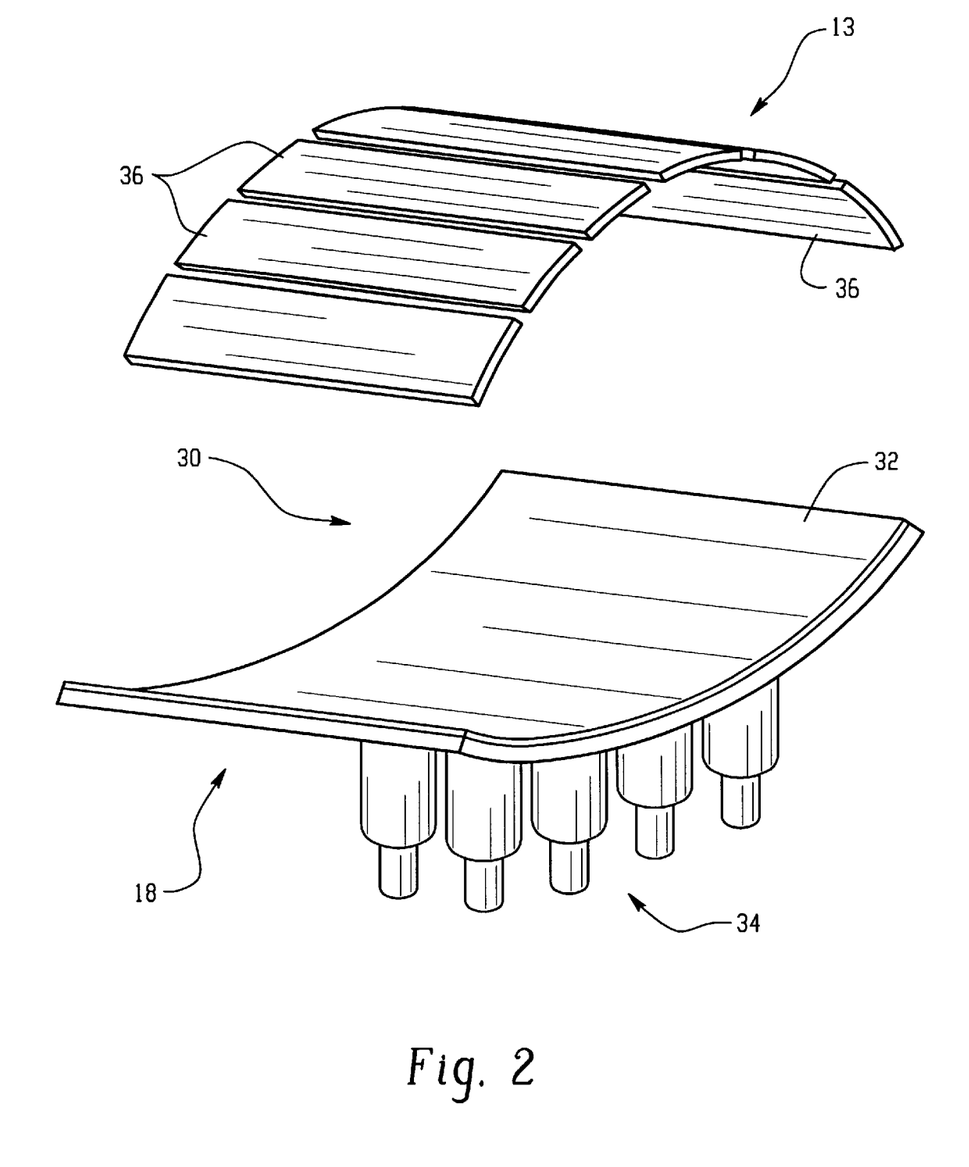
FIG. 2 is a perspective view of the upper and lower gamma camera detectors.

Turning to FIG. 2, the lower detector 18 has a curvature corresponding to the curvature of the patient receiving surface 22. The lower detector 18 includes a sheet of scintillating material 32 such as sodium iodide (NaI). Radiation interacts with the scintillator 32 to produce scintillations or flashes of light. An array of photodetectors 34 such as photomultiplier tubes (PMTs) in optical communication with the scintillator 32 converts the flashes of light into electrical signals for further processing. In an embodiment suited to both positron coincidence (511 keV) and single photon imaging, the scintillating crystal 32 is approximately 30 mm (1.18 inch) thick.

The upper detector 13 includes a plurality (six in the illustrated embodiment) of discrete detector portions 36 disposed in an arc about the examination region 30. In one embodiment, the each detector portion 36 is 80 cm (31.5 inch) long by 15 cm (5.9 inch) wide. The arc preferably subtends an angle about the examination region 30 of at least 45 degrees.

Figure 3:
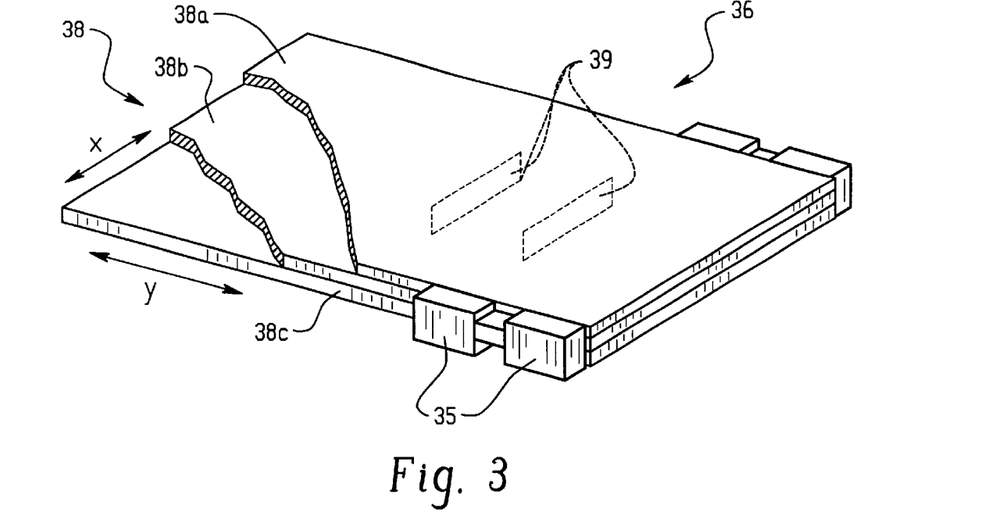
FIG. 3 is a perspective view of an upper detector portion.

Turning now to FIG. 3, each of the detectors 36 includes a planar, multi-layer (three in the disclosed embodiment) scintillating material 38 such as NaI. The layers are of varying thickness and arranged so that relatively thinner layers are disposed relatively closer to the examination region 30. In the illustrated embodiment, the thinnest layer 38a has a thickness of 6 mm (0.24 inch) and is located nearest the subject, the thickest layer 38c has a thickness of 12 mm (0.48 inch) and is located furthest therefrom, and a layer 38b having a thickness of 8 mm (0.31 inch) is located therebetween. The relative layer thicknesses are selected so that the scintillation interactions for gamma radiation of a desired energy (e.g., 511 keV) are distributed substantially equally in the various layers 38a, 38b, 38c of the crystal. Light baffles 39 may be included if desired to improve the accuracy of the y position signals.

Figure 4:
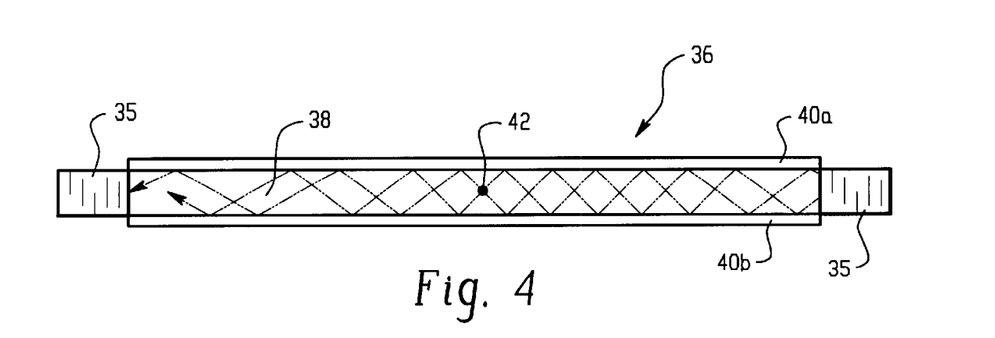
FIG. 4 is a side view of an upper detector portion.

Turning now to FIG. 4, each layer of the crystal 38 is sandwiched between a corresponding pair of light reflective surfaces 40a, 40b which direct the light generated by a scintillation interaction 42 to the edge of the crystal 38.

With reference to FIGS. 3 and 4, each detector 36 also includes an array of photodectors 35 such as low profile position sensitive photomultiplier tubes (PSPMTs) disposed along the sides of each detector 36, with the segments of the PSPMTs 35 in optical communication with the layers 38a, 38b, 38c of the scintillator. Again, the PSPMTs convert flashes of light from the scintillator into electrical signals for further processing.

Figure 5:
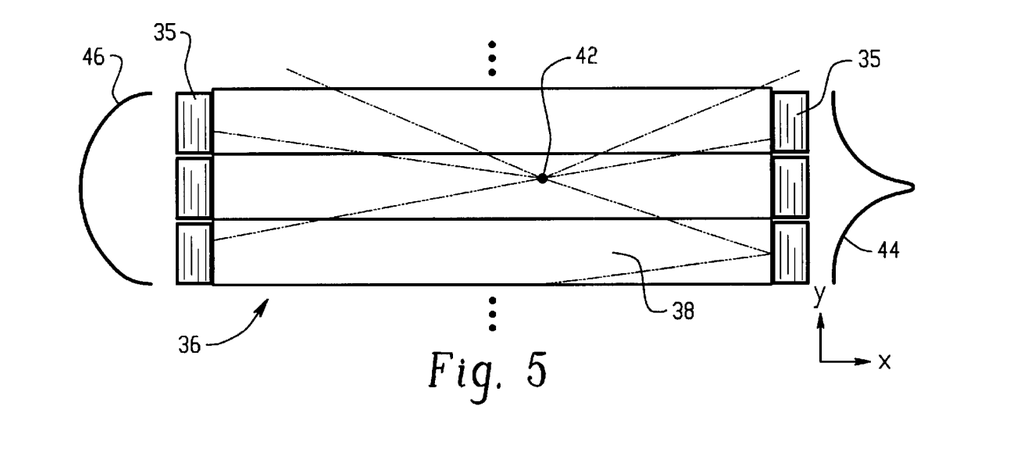
FIG. 5 is a top view of an upper detector portion.

Turning to FIG. 5, an exemplary scintillation interaction 42 occurs at position x,y. As depicted by the curves 44, 46, the intensity of the light received by the PSPMTs is a function of their position relative to the y coordinate of the interaction. Moreover, the shape of the curve is a function of the distance between the interaction 42 and the PSPMTs. Interactions occurring relatively near an edge of the scintillator 38 are characterized by a relatively sharp peak 44, whereas interactions occurring relatively far from the edge of the detector are characterized by a relatively flat peak 46. Thus, the PSPMT outputs can also be used to determine the x position of the interaction. The x,y position determination may be made as described in U.S. Pat. No. 5,813,983 entitled Depth-of-Interaction and Other High Order Moments Filtering for Improved Detection in Thick Scintillation Crystals, expressly incorporated by reference herein, where the zero-th moment is a measurement of energy, the first moment is a measurement of the y position, and the second moment is indicative of the x position.

Returning to FIG. 1, the injection and monitoring device 20 receives a patient's arm. The device 20 supports a needle for receiving blood samples and/or for injecting agents such as radiopharmaceuticals, heart beat acceleration and control agents, other pharmacokinetics agents, and other medications. Insertion of the needle may be accomplished manually or automatically. Suitable controls and valves may be provided to allow both input and outputs or provide a plurality of outputs (e.g., for multiple blood samples) or inputs (e.g., radiopharmaceuticls, medication). The device may also provide information on patient blood pressure. A thermistor to be placed in a patient's mouth for monitoring the respiration cycle may also be provided.

Figure 6:
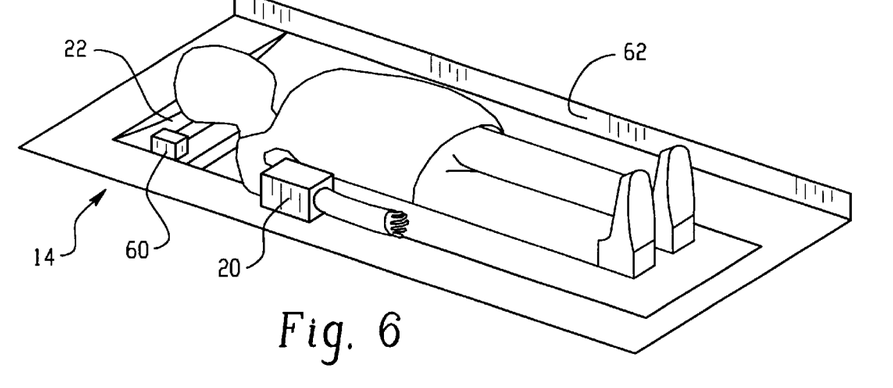
FIG. 6 depicts an optical scanning mechanism.
Figure 7:
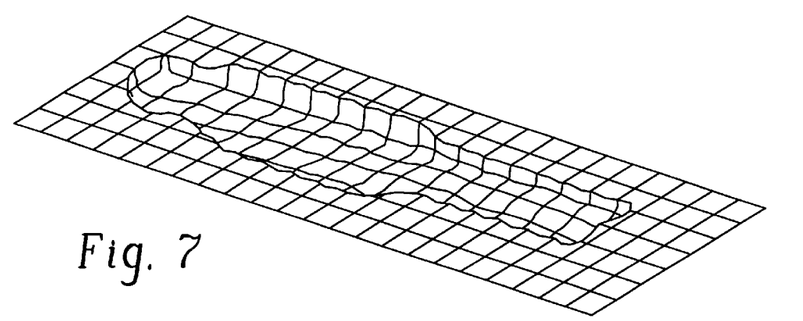
FIG. 7 depicts a negative profile of an object.

The object receiving surface 22 includes a pressure sensitive material whose impedance varies as a function of the pressure applied at various points on the surface. Alternately, a scanning light source 60 disposed along one side of the patient receiving surface 22 and corresponding detectors 62 may be used. (See FIG. 6) This information can be used in various ways, such as estimating an object's weight and weight distribution, estimating the distance between the surface and the object in areas where there is no contact with the surface, and determining a spatial distribution of the points of contact between the object and the surface 18. An objective of the latter is to create at least a partial profile of the bottom portion of the object as depicted in FIG. 7.

Figure 8:
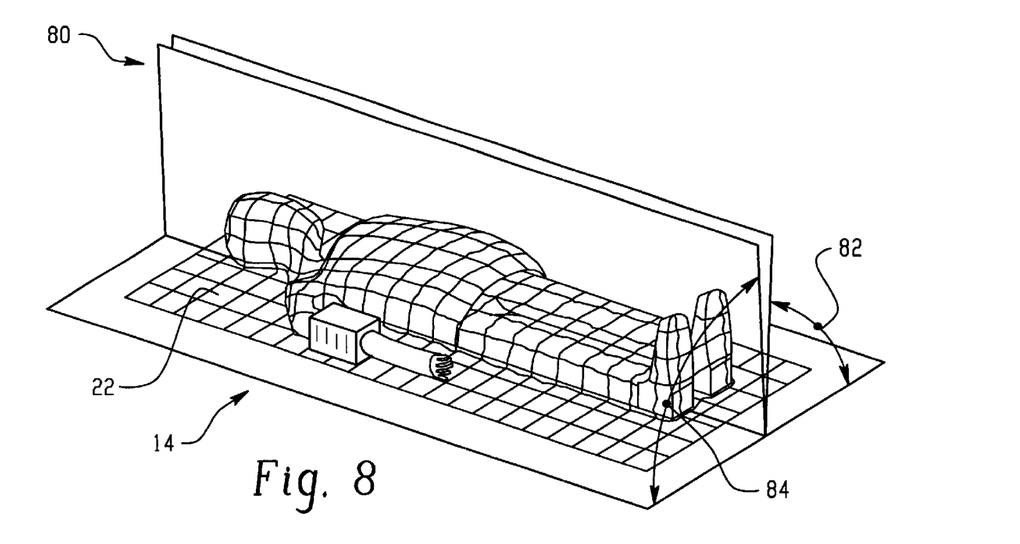
FIG. 8 is depicts an ultrasound scanning device.

With reference to FIG. 8, profile information may be provided by way of an ultrasound device 80 which is mounted to the gamma camera 10 and pivotable about the object as shown by arrows 82, 84. With the upper detector 13 retracted, the ultrasound device 80 may be swept to over the object, with the received ultrasound data used to provide profile information as to the top portion of the object. Rather than being pivotable, the ultrasound device 80 may be translatable in the longitudinal and/or transverse directions.

Returning again to FIG. 1, a transmission radiation source 19 is disposed on the outside of the upper detector 13. The transmission source contains a source of medium or high energy radiation such as 133-Ba or 137-Cs, which produce mainly 356 keV and 662 keV gamma radiation respectively, although other suitable sources may also be used. The source 19 is movably mounted with respect to the lower gantry 12 so as to permit scanning of the object along an arc about the upper portion of the object support 14 as well as longitudinally along the long axis of the patient at a plurality of angles along the arc. The drive mechanism for the source 19 is preferably operable independently from that of the upper detector 13 so that the source 19 is operable with the detector 13 located in either its operating or retracted positions.

Figure 9:
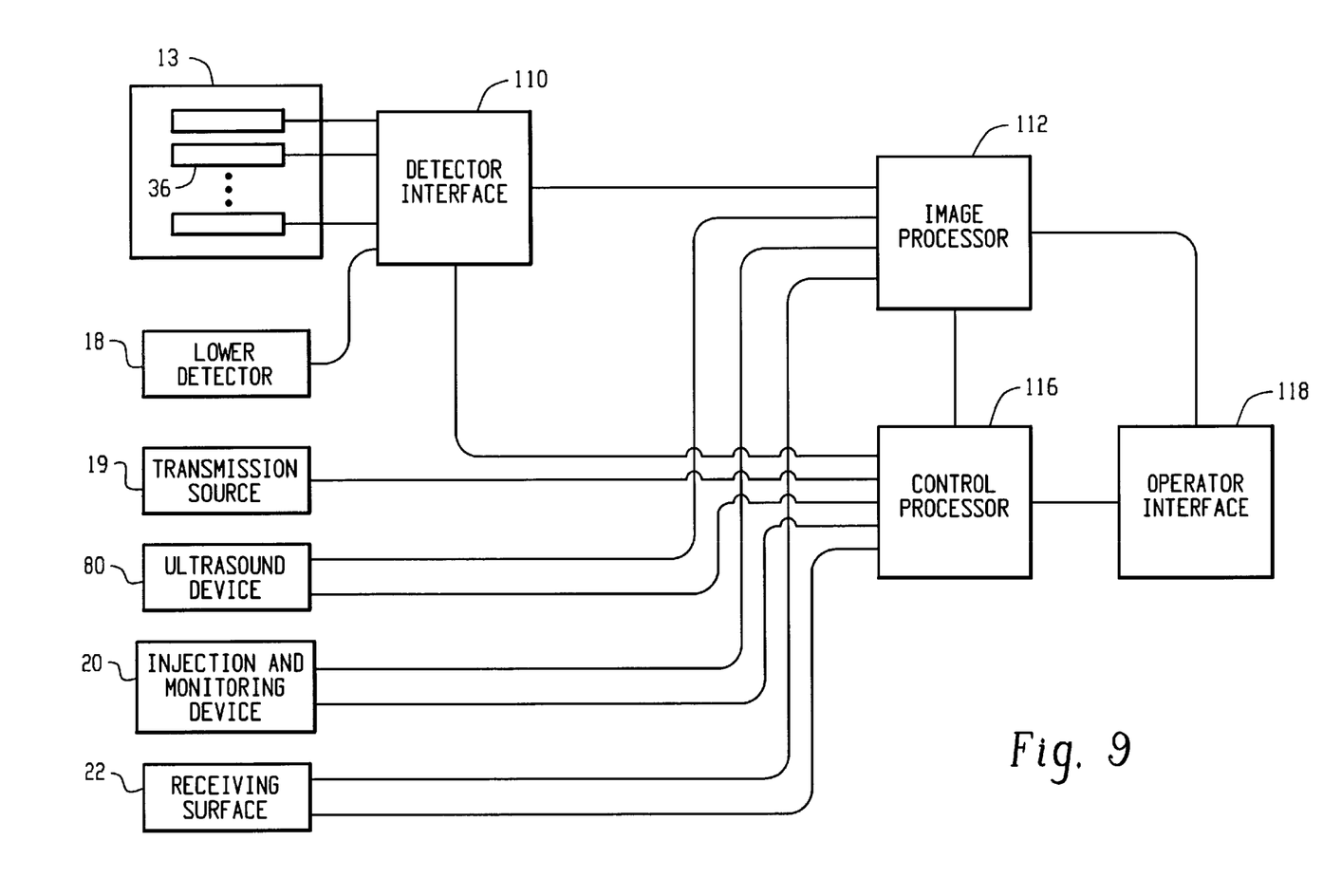
FIG. 9 is a functional block diagram of a gamma camera.

Turning to FIG. 9, a detector interface 110 processes the electrical signal from the upper 13 and lower 18 detectors to determine the position and energy of detected events. The detector interface 110 includes a coincidence processor for determining whether detected events are indicative of positron annihilation events. More particularly, the coincidence processor determines whether events are detected an upper detector portion 36 and the lower detector 18 within a coincidence time window. One or more of the detector portions 36 and respective scintillator layers 38a, 38b, 38c may be selectively disabled and enabled. Data indicative of valid events is stored for further processing by the image processor 112.

The transmission source 19 operates under the direction a controller 116. Requisite drive mechanisms associated with the source 19 cause the desired scanning motion and control the emission of the transmission radiation. Similarly, requisite drive mechanisms associated with the ultrasound device 80 cause the requisite scanning motion of the device; and appropriate valves and controls cause the operation of the injection and monitoring device 20, both under control of the controller 116. Signals from the ultrasound device 80, injection and monitoring device 20, and receiving surface 22 are received by the image processor 112. Moreover, the controller 116 may use status and other signals from the foregoing devices to coordinate the operation of the gamma camera system.

The image processor 112 uses data from the detector interface 110 to generate images indicative of the radionuclide decays detected by the detectors 13, 18. Emission radiation from the object is reconstructed to create human readable images using single or multiple slice rebinning, filtered back projection, iterative reconstruction, focal plane imaging, or other techniques. Transmission radiation detected during operation of the transmission source 19 may be used to attenuation correct the emission images. The reconstructed images and other pertinent information are displayed on the operator interface 118.

In operation, the upper detector 13 is retracted and the transmission source 19 and ultrasound device 80 are located so as to facilitate ingress of the patient. A suitable radiopharmaceutical such as or FDG or 99m-Tc is administered to the patient, either using injection device 20 or manually. Once the patient has been properly situated, the upper detector 13 is returned to its operating position.

The detector interface 110 processes data from the detectors 13, 18 to determine the position, energy, and if desired the depth-of-interaction of the detected events. In positron imaging, the coincidence processor determines whether the detected events are indicative of positron annihilations. The image processor 112 generates a human readable image for display on the operator interface 118.

Figure 10:
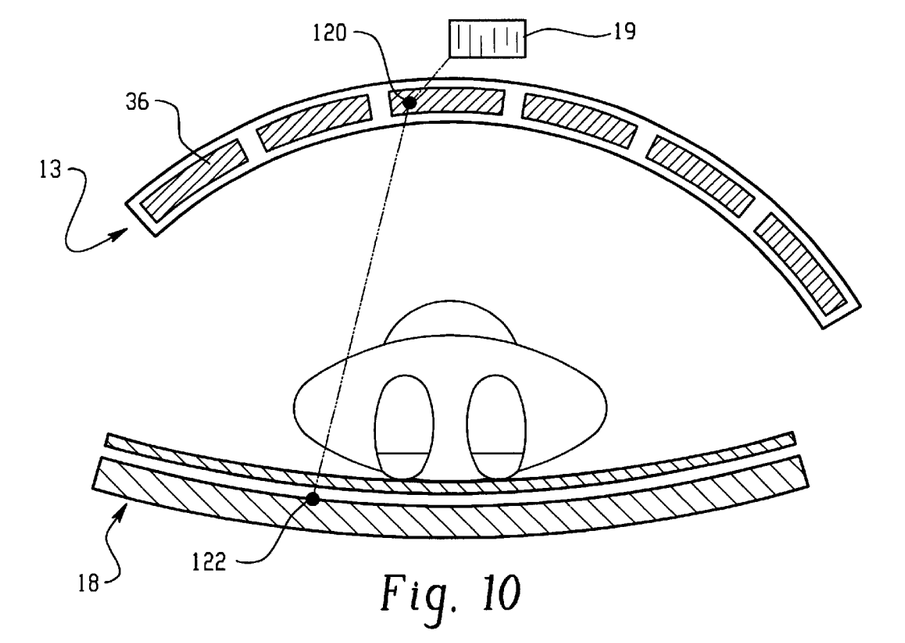
FIG. 10 illustrates the imaging physics geometry of a gamma camera.

Transmission information may also be provided. According to one technique, the transmission radiation source 19 may be activated with the upper detector 13 in its operating position. With reference to FIG. 10, this mode of operation takes advantage of Compton scattering in the upper scintillators 38 to so that singles transmission radiation may be detected in a coincidence mode. The transmission source is scanned across the upper surface of the upper detector 13, for example longitudinally along one of the detector portions 36. As the source is scanned across the detector, transmission radiation from the source 19 undergoes Compton scattering in the scintillator 38 and is detected as an event by the respective detector portion 36 as depicted by exemplary event 120. The Compton interaction also generates a lower energy gamma. This lower energy gamma may in turn interact with the lower detector 18 and be detected as an event as depicted as exemplary event 122. Inasmuch as the two events 120, 122 are substantially temporally simultaneous, they may be treated and detected as a coincidence event.

Returning momentarily to FIG. 3, events detected by the outer layer 38c are more likely to represent Compton scatter of the transmission radiation than emission radiation from the patient, whereas events detected by the inner layers are less likely to represent transmission radiation and more likely to represent emission radiation. Accordingly, events detected in the inner 38a and middle 38b layers of the respective detector portion 36 are disregarded. Alternately, events detected by the middle 38b layer may also be used. In any case, coincident events detected by the respective upper detector portion 36 and the lower detector 18 are treated as indicative of transmission events and rebinned accordingly. Inasmuch as the Compton scattered gamma is known to have traveled along the line having endpoints at 120 and 122, attenuation along that path can be estimated if, as in other transmission imaging techniques, a ratio of intensity with and without the object is created for that particular path. The intensity profiles without the object or patient depend only on the source strength and the detector geometry and can consequently be acquired beforehand and is referred to as "blank scan" in the prior art. A particular advantage of this technique is that, because the path traveled by the transmission radiation is determined by the position of the detected events; the technique does not require that the position of the transmission source 19 be known precisely.

After the source has been moved longitudinally over one of the upper detectors 36, the source is moved to a position over another of the upper detectors 36 and the process is repeated. It should be noted that, during operation of the transmission source, events detected by the other detector portions 36 are assumed to be indicative of emission radiation and are processed normally.

The transmission data is then reconstructed to generate an attenuation map of the patient. This information may be used by the image processor to provide an attenuation corrected emission image or displayed in a human readable form.

Figure 11:
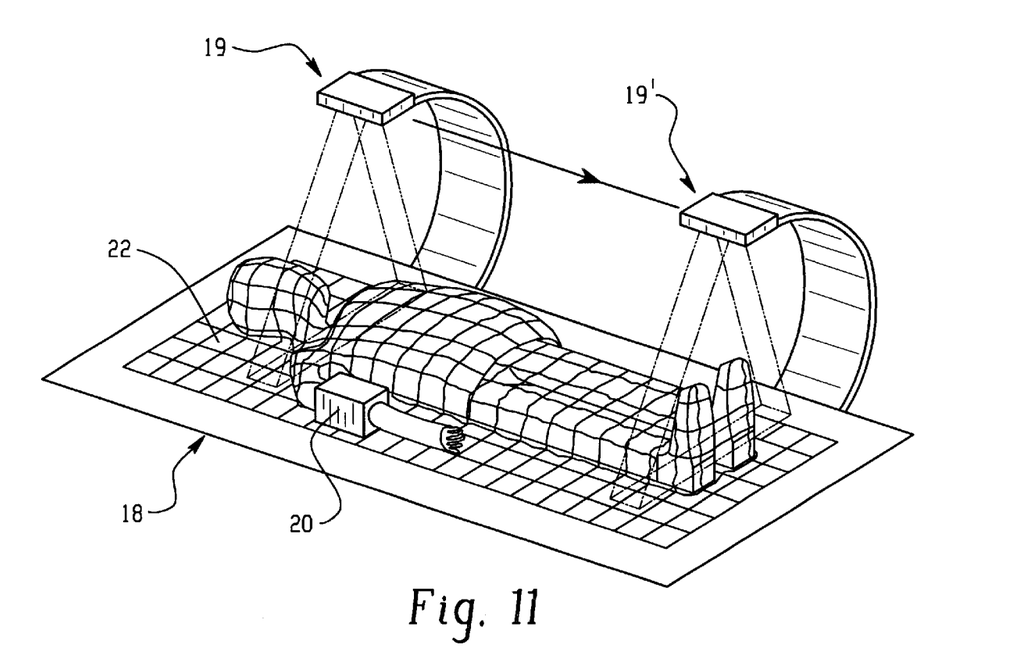
FIG. 11 illustrates operation of a transmission radiation source.

With reference to FIG. 11, the transmission source 19 may be activated with the upper detector 13 in its retracted position. When activated, the source is scanned across the object as shown by exemplary positions 19 and $19^1$ and detected by detectors 18. This information can be used to generate a shadowgraphic image of the object. One application of this information is to identify, either by the physician or automatically, more precisely those regions where the object can be reasonably modeled as a uniform medium and those regions where a more complete transmission scan (for example using the Compton scattering technique described above) is needed. The data may also be used to identify fiducial points or landmarks such as the tip of the cranium, clavicle, sternum, patellas, other visible points for image registration purposes.

The control processor 116 preferably controls and/or monitors the status of the injection and monitoring device 20 to ensure coordination of the injection and monitoring device 20 and the imaging process.

Figure 12:
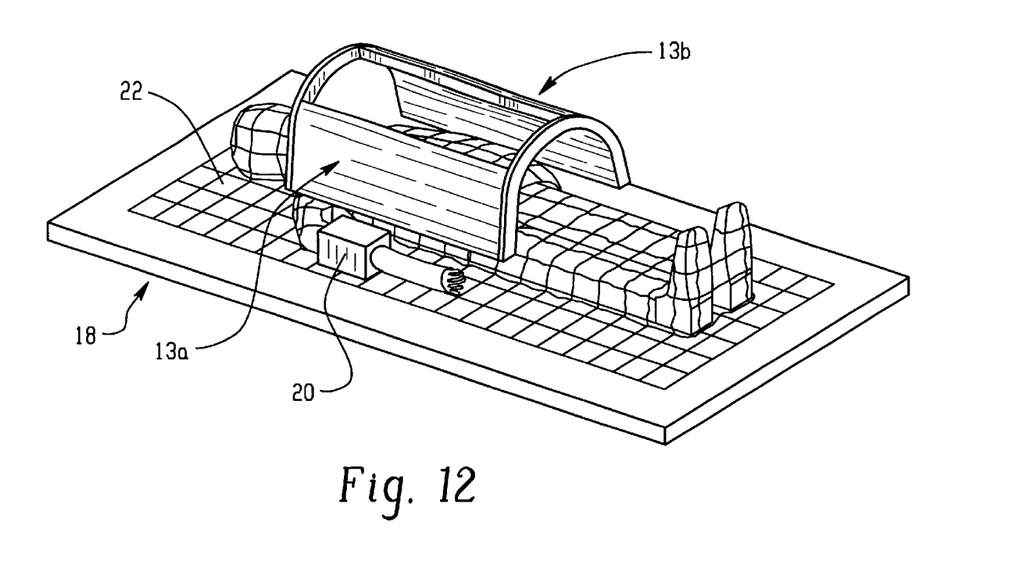
FIG. 12 is a perspective view of a split detector.
Figure 13:
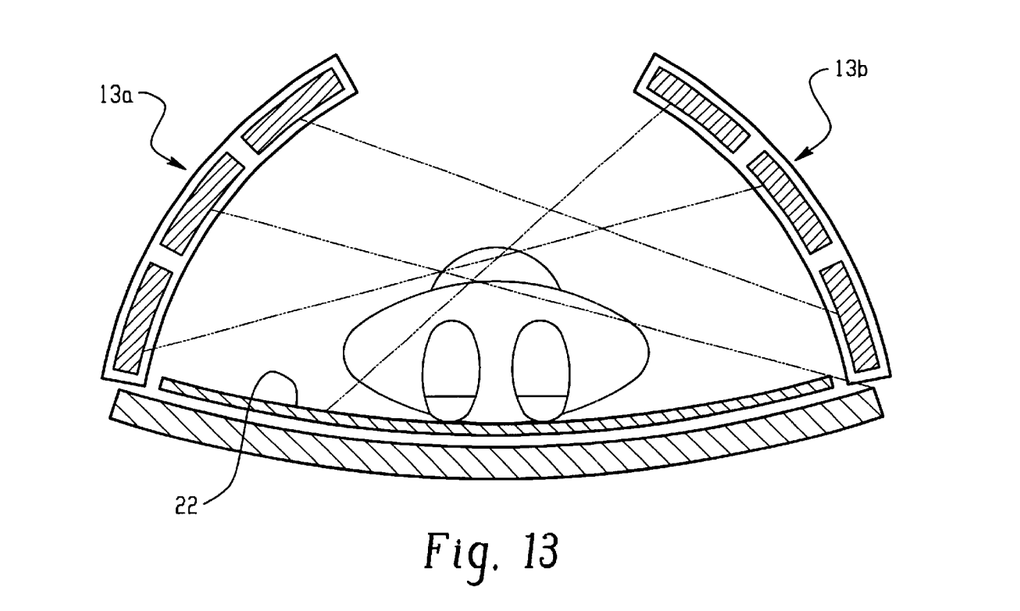
FIG. 13 illustrates the imaging physics geometry of a split detector configuration.

FIG. 12 depicts an alternate embodiment which includes a split upper detector. The upper detector may be operable as described above and also selectively physically separable into first 13a and second 13b portions. Once data has been collected as described above, the detectors may be physically separated and additional data collected. With reference to FIG. 13, a particular advantage to this aspect of the invention is that, for a detector of a given size a more complete tomographic data set may be obtained.

While the foregoing description has focused primarily on positron imaging, it will be appreciated the present invention also contemplates single photon imaging. Of course, the detectors would preferably be fitted with appropriate collimators. In relatively low energy imaging, the signals from one or more of the outer scintillator layers 38b, 38c layers are preferably disregarded. Nonetheless, the transmission detection may be Aaccomplished using the Compton scattering technique as described above simultaneously with the low energy emission. Alternately, transmission data may be obtained directly with the upper detector 13 located in its retracted position. It will also be appreciated that transmission sources other than 133-Ba may be used. Scintillator materials other than NaI, for example BGO, may also be employed.

The gamma camera 10 may be arranged vertically so that a patient is scanned in a standing, rather than supine, position. Alternately, the gamma camera may be mounted near the bore of a computed tomography or magnetic resonance scanner, radiation therapy device, or the like so that the patent may be readily introduced into the imaging region thereof by moving the patient receiving portion 22 in the longitudinal direction on rollers or the like.

The invention has been described with reference to the preferred embodiments. Obviously, modifications and alterations will occur to others upon reading and understanding the preceding description. It is intended that the invention be construed as including all such modifications and alterations insofar as they come within the scope of the appended claims or the equivalents thereof.

What is claimed is:

1. A gamma camera comprising:
    a fixed detector having a radiation sensitive face which faces an examination region;
    a movable second detector including a plurality of discrete detector portions each having a radiation sensitive face which faces the examination region, the second detector being movable between a first position opposite the examination region from the fixed detector for detecting radiation from the examination region and a second position for facilitating ingress of an object into the examination region.

2. The gamma camera of claim 1 wherein the discrete detector portions include
    an elongate scintillator;
    a plurality of photodetectors disposed along a first edge of the scintillator;
    a plurality of photodetectors disposed along a second edge of the scintillator, the second edge being opposite the first edge.

3. The gamma camera of claim 2 wherein the elongate scintillator comprises a plurality of scintillator layers and including photodetector means for detecting scintillations occurring in each of the layers.

4. The gamma camera of claim 2 including first and second moment processors operatively connected to the photodetectors for determining x,y positions of the scintillations.

5. The gamma camera of claim 1 further including a transmission radiation source which emits radiation which interacts with the second detector to produce Compton scattered photons, at least a portion of which photons pass through the examination region and are received by the first detector, the second detector when in its first position being disposed between the transmission source and the examination region.

6. The gamma camera of claim 5 further including means for translating the transmission radiation source along each of the discrete detector portions.

7. The gamma camera of claim 5 wherein the transmission radiation source includes one of 133-Ba and 137-Cs.

8. The gamma camera of claim 1 including coincidence detection for determining whether radiation detected by the fixed detector and the detector portions of the second detector is coincident.

9. The gamma camera of claim 1 further including a pressure sensitive surface disposed between the fixed detector and examination region which surface provides a signal indicative of a pressure applied to the surface.

10. The gamma camera of claim 1 including
    means for determining a region of the object which can be modeled as a uniform medium; and
    means for generating an attenuation map of a second region of the object.

11. A gamma camera comprising:
    a first detector having a radiation sensitive face which faces an examination region;
    a second detector disposed opposite the examination region from the first detector, the second detector including a first radiation sensitive face which faces the examination region and a second radiation sensitive face;
    a transmission radiation source for emitting transmission radiation which is received by the second radiation sensitive face of the second detector, said transmission radiation interacting with the second detector to produce Compton scattered photons which are received by the first detector; and
    means for determining whether transmission radiation received by the second detector and Compton scattered photons received by the first detector are coincident.

12. The gamma camera of claim 11 wherein the second detector comprises a plurality of elongate detector portions disposed in an arc about the examination region, wherein the detector portions include a scintillator and a plurality of photodetectors for receiving light which has reached first and second edges of the scintillator.

13. The gamma camera of claim 11 wherein the second detector includes a scintillator having a plurality of layers and a plurality of photodectors for receiving signals indicative of scintillations occurring in each of the layers and further including means for selectively disregarding signals from at least one of the layers during operation of the transmission radiation source.

14. The gamma camera of claim 12 including a first scintillator layer, the scintillator layer being disposed between a pair of light reflective surfaces which cause light generated within the crystal to be reflected to an edge thereof.

15. The gamma camera of claim 11 including means for disregarding signals from a layer nearest the examination region while accepting signals from a layer nearest the transmission source.

16. The gamma camera of claim 11 wherein the second detector is movable between a first position for detecting radiation from the examination region and a second position for facilitating ingress of an object into the examination region.

17. The gamma camera of claim 16 including means for scanning the transmission source across the second radiation sensitive face of the second detector when the second detector is in the first position.

18. The gamma camera of claim 17 including means for scanning the transmission source longitudinally with respect to the examination region when the second detector is in the second position.

19. A method comprising:
    using a fixed radiation sensitive detector to detect gamma radiation from an examination region;
    using a second detector to detect gamma radiation from the examination region, the second detector including a plurality of discrete detector portions each having a first radiation sensitive face which faces the examination region, the second detector being movable between a first position for detecting radiation from the examination region and a second position for facilitating ingress of an object into the examination region;
    determining whether the radiation detected by the first and second detectors is indicative of positron annihilation events; and generating an image indicative of the detected positron annihilation events.

20. The method of claim 19 wherein the discrete detector portions include a second radiation sensitive face and including the steps of provimg transmission radiation which is received by the second radiation sensitive face of a discrete detector portion, said transmission radiation interacting with the discrete detector portion to produce Compton scattered photons which interact with the first detector;

using the discrete detector portion to detect the interactions;

using the first detector to detect radiation incident thereon;

determining whether radiation received by the discrete detector portion and Compton scattered photons received by the first detector are coincident;

using the coincident radiation to provide an attenuation corrected image of the detected positron annihilation events.

21. The method of claim 20 including repeating the steps of providing, using the discrete detector portion, using the first detector, and determining for a plurality of the discrete detector portions.

22. The method of claim 20 wherein the discrete detector portion includes a plurality of scintillator layers and including disregarding interactions between the transmission radiation and at least one of the layers.

23. The method of claim 19 wherein the second detector includes a scintillator having first and second edges, interactions between the radiation and the scintillator generating light, the method including using photodetectors to detect light which has reached the edges and determining locations of the interactions.

24. The method of claim 23 including determining the first and second moments of the detected light.

25. The method of claim 19 including moving the second detector to a retracted position and using an ultrasound device to scan a portion of the object.

* * * * *